Figure 1:
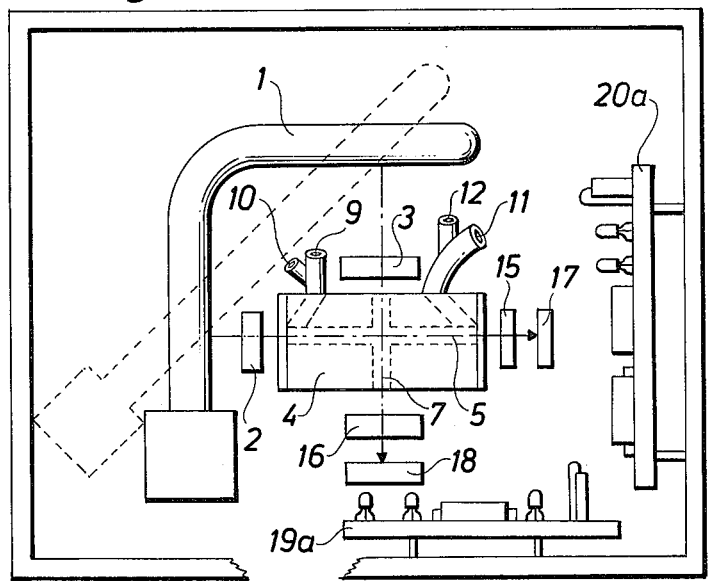

United States Patent [19]
Andrén et al.

[11] 4,099,882
[45] Jul. 11, 1978

[54] APPARATUS FOR OPTICALLY ANALYZING FLUIDS

[75] Inventors: Lars-Göran Hjalmar Andrén; Rune Harald Björkman, both of Upsala, Sweden; Richard Lee Easterday, Martinsville, N.J.; Hans Gösta Munktell, Upsala, Sweden

[73] Assignee: Pharmacia Fine Chemicals AB, Upsala, Sweden

[21] Appl. No.: 731,870

[22] Filed: Oct. 13, 1976

[30] Foreign Application Priority Data

Oct. 29, 1975 [SE] Sweden ............................... 7512125

[51] Int. Cl.² .................. G01J 3/50; G01N 21/26; G01N 1/10
[52] U.S. Cl. ..................................... 356/181; 356/183; 356/184; 356/206; 356/246; 250/575
[58] Field of Search ................ 356/73, 181, 201, 204, 356/205, 206, 246, 180, 184, 188, 195, 183; 250/575, 576, 578

[56] References Cited

U.S. PATENT DOCUMENTS

| | | | |
|---|---|---|---|
| 3,463,927 | 8/1969 | Allington | 356/206 |
| 3,506,367 | 4/1970 | Ross et al. | 356/246 |
| 3,625,621 | 12/1971 | Field | 356/206 |
| 3,751,173 | 8/1973 | Sanz et al. | 356/246 |
| 3,810,695 | 5/1974 | Shea | 356/73 |

*Primary Examiner*—Vincent P. McGraw
*Attorney, Agent, or Firm*—Seidel, Gonda & Goldhammer

[57] ABSTRACT

In optical analysis of fluids a method and an apparatus are described by which it is possible to continuously measure the concentration value of the fluid within a very broad range of concentration values. In one single test glass optical paths of different lengths are provided substantially perpendicularly to each other. The concentration value of the fluid is measured simultaneously along the two mutually perpendicular optical paths.

19 Claims, 8 Drawing Figures

APPARATUS FOR OPTICALLY ANALYZING FLUIDS

The present invention relates to a method and an apparatus for optically analyzing fluids.

Radiation from a source of radiation is passed through a container filled with a test fluid containing a dissolved substance the concentration of which is to be determined. Knowing the intensity of the radiation prior and after its passage through the test fluid and also knowing the distance passed by the radiation through the test fluid the analyst will be able with the aid of the Beer-Lambert law to determine the concentration of the test fluid. The absorbency, i.e. log $Po/P$ where $Po$ is the intensity of the radiation prior to and $P$ is the intensity of the radiation after passage through the test fluid, is according to said law directly proportional to the concentration of the test fluid and the distance passed by the radiation through the test fluid. Known photometers permit measuring with a maintained good degree of exactitude of concentrations corresponding to absorbency values up to 2 units whereas specific measuring methods must be applied in case higher concentrations are to be measured. A known method of this type comprises transferring the test fluid into a new test glass in which the distance passed by the radiation through the test fluid is considerably reduced, thereby permitting measurement of higher concentrations while holding the measured absorbency value at or below 2 units. However this is a cumbersome procedure which in addition has the inherent drawback that the concentration of the test fluid can not be measured continuously. The purpose of the present invention is to overcome this drawback by enabling the concentration values of the test fluid to be registered simultaneously within, on the one hand, a first sensitivity range for lower concentrations and, on the other hand, a second sensitivity range for higher concentrations.

In connection with the optical analysis of fluids containing several components it is known to examine the test fluid by causing radiation of different, predetermined wave lengths to pass therethrough. In accordance with such an examination procedure filters for different wave lengths are successively placed between the light source and the test glass containing the test fluid. The present invention is based on measuring the concentration of the test fluid simultaneously at two wave lengths.

In connection with the optical analysis of the fluids it is also known to compensate variations of the intensity of the light source by providing a reference fluid of known concentration in one flow duct and the test fluid containing the substance the concentration of which is to be determined in a second flow duct. Both flow ducts are passed by radiation emitted from the same point of the light source. This double flow duct technique is used according to the present invention while simultaneously the above-mentioned advantages are obtained.

Figure 2:
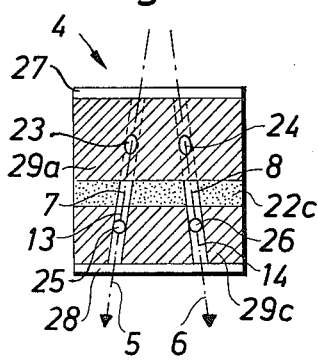
Figure 3:
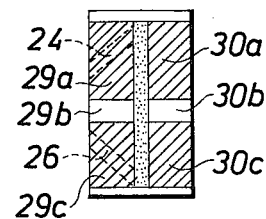
Figure 4:
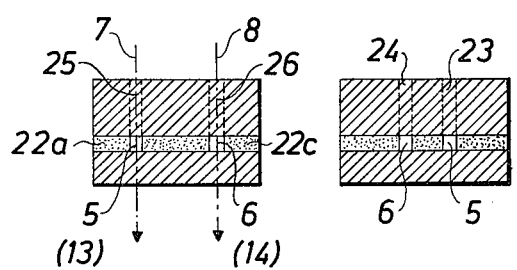
Figure 5:
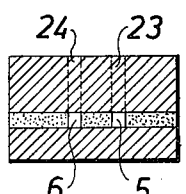
Figure 7:
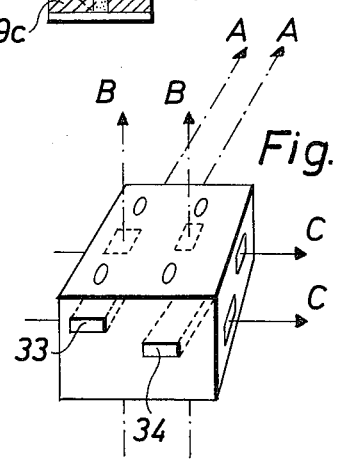
Figure 6:
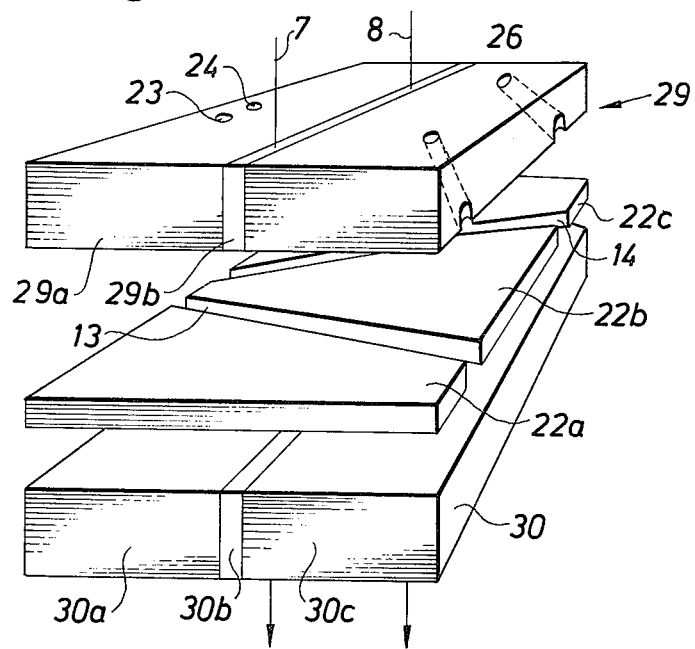
Figure 8:
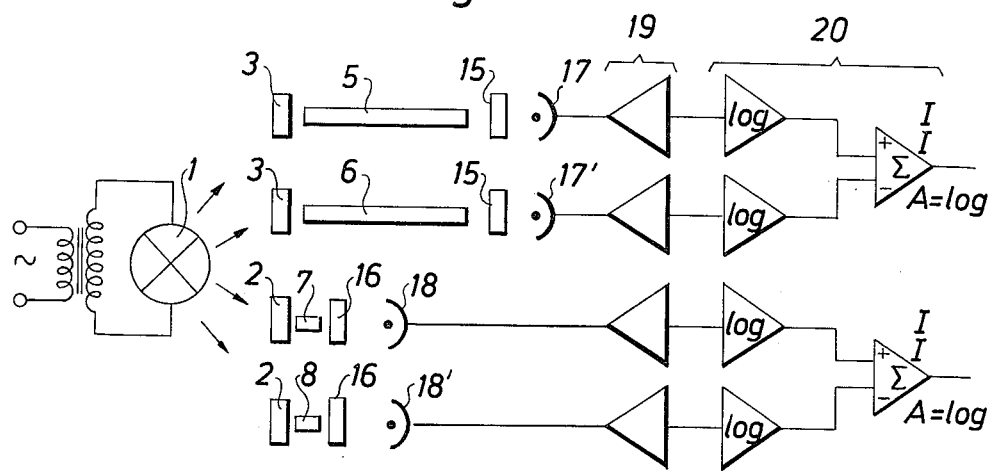

The characteristic features of the invention appear from the attached claims. An embodiment of the invention will be described in detail hereafter by reference to the attached drawings in which FIG. 1 is an elevation of an apparatus for optical analysis of a fluid in accordance with the present invention, FIG. 2 is a top view of a through-flow test glass used in the apparatus shown in FIG. 1, FIG. 3 is an elevation of the through-flow test glass shown in FIG. 2, FIG. 4 is a rear elevation of the test glass shown in FIG. 2, FIG. 5 is a front elevation of the test glass shown in FIG. 2, FIG. 6 is a perspective view of the test glass shown in FIG. 2 with certain portions removed and certain main components shown in exploded view, FIG. 7 is a perspective view of a second embodiment of a test glass adapted to be used in an apparatus according to the invention, and FIG. 8 is a block diagram of the device according to the invention.

According to FIG. 1 the apparatus according to the invention comprises a radiation source 1 constituted by an angularly deformed discharge tube. The discharge tube 1 may also be straight as indicated by broken lines in FIG. 1. The discharge tube may, for example, be of the mercury type, iodine type, hydrogen type etc. The radiation from one point of the radiation source passes through a fluorescence converter 2 emitting radiation of a certain wave length which is permitted to pass through a test glass 4 along a first pair of optical paths 5 and 6. Radiation from a different point of the radiation source is passed through a fluorescence converter 3 emitting radiation of a certain wave length which is permitted to pass through test glass 4 along a second pair of optical paths 7 and 8. The fluorescence converter 2, for example, may comprise two separate converters, one for each path 5 and 6. Alternatively the fluorescence converter 2 may be common to both optical paths 5 and 6. The same applies to fluorescence converter 3. In any case these fluorescence converters are not essential for the invention and may be omitted. The first pair of optical paths comprises two extended paths 5 and 6 (compare FIG. 2) whereas the other pair comprises two short paths 7 and 8. These pairs of optical paths are provided substantially prependicularly to each other. In the example shown a test fluid enters through an inlet tube 9, passes through the test glass in a flow duct 13 and is discharged from the test glass through an outlet tube 12. The optical paths 5 and 6 thus substantially are formed by flow ducts 13 and 14 provided in the test glass. The optical paths 7 and 8 extend transversely to the longitudinal extension of flow ducts 13 and 14. In the example shown ducts 13 and 14 converge towards a common point on the discharge tube 1. However this is not necessary. Instead, the ducts may be mutually parallel and radiation from the same point of the radiation source may be provided by an optical lens. The same applies to the light along optical paths 7 and 8. Filters 15 and 16 of suitable wave lengths are provided at the radiation exit ends of the optical paths 5, 6 and 7, 8 respectively. Filter 15, for example, may comprise two separate filters, one for each of paths 5 and 6. Alternatively the filter may be common for both optical paths 5 and 6. The same applies to filter 16. At any event these filters are not essential for the invention and may be omitted. After having passed filters 15 and 16 respectively, if provided, the radiation at the exit end of each of the four optical paths 5, 6, 7 and 8 reaches one photocell each, photocell 17 for the optical path 5 and photocell 18 for the optical 7 being shown in FIG. 1. In FIG. 8 the corresponding photocell 17' for the optical path 6 and photocell 18' for the optical path 8 are shown. As appears from FIG. 8 individual amplifiers 19 are coordinated with each of the four photocells for amplification of the respective photocell current. These amplifiers 19, as shown in FIG. 1, are mounted on a circuit card 19a. The outlet signals from amplifiers 19 belonging to photocells 17 and 17' are passed through a logarithm-forming circuit 20 emitting a voltage which is proportional to the logarithm of quotient of the intensity of the radiation received, on the one hand, in duct 13 containing the reference fluid and, on the other hand, in duct 14 containing the test fluid. This logarithm-forming circuit is known in itself and does not form part of the present invention. For example use may be made of the logarithm-former marketed by the American firm Analogue Devices Inc. (seated in Norwood, Mass.) under the type designation 756/P. In a corresponding way by means of a corresponding logarithm-forming circuit 20 there is formed the logarithm of the quotient between the intensity of the radiation after passage through, on the one side, the optical path 7 and, on the other side, the optical path 8. These logarithm-forming circuits are provided on a circuit card 20a. Thus, the output signals from each of the two logarithm-forming circuits 20 are an individual measure of the concentration of the dissolved substance in the test fluid. The output signals from each of the logarithm-forming circuits may, for example, be passed through a continuously operating writer or may be recorded in any other suitable way.

In an embodiment of the invention the extended optical paths 5 and 6 have a length of 20 mm whereas the short optical paths 7 and 8 have a length of only 1 mm. If the fluorescence converters and filters are tuned to the same frequency, the apparatus has two sensibility ranges, a first sensibility range relating to measurements along the extended optical paths 5 and 6 and a second sensibility range relating to measurement along the short optical paths 7 and 8. At low to moderate concentrations of the dissolved substance in the test fluid the measuring results from paths 5 and 6 are used yielding high exactitude of the measurement at concentrations corresponding to absorbency values up to about 2 units (absorbency values $A = kcl$; where $k$ = constant, $c$ = concentration of the dissolved substance, $l$ = the distance passed by the radiation through the substance). At high concentrations the influence of the scattered light on the measuring result will be prohibitively strong when measurements are performed along paths 5 and 6. Measurements are then performed along paths 7 and 8 causing the measured absorbency values for the same concentration of the dissolved substance in the embodiment described now to be 20 times lower. Thus, by simultaneously measuring the concentration value along the two mutually perpendicular optical paths, it will be possible continuously to measure a very broad range of concentration values.

The fluorescence converters 2 and the corresponding filters 15 may be tuned to a certain wave length, whereas fluorescence converters 3 and corresponding filters 16 may be tuned to another certain wave length. By simultaneously taking absorbency measuring values for the test solution it is now possible to find the mutual concentration ratio between two components in the test fluid (provided that it is known that the components in question have absorbency value peaks at the selected wave lengths). Thereby it is possible to measure with maximum sensitivity the concentration of these two components. The refinement provided by the present invention resides in that this measurement is performed simultaneously at the different wave lengths. This is of particular importance in such cases where the concentration of the various components of the test liquid changes with time, such as, for example, is the case in column separation.

The through-flow test glass used in the shown embodiment of the invention is illustrated in detail in FIGS. 2 – 6. The test glass has the shape of a parallelepiped and is made of quarts glass. Three black glass sheets 22a–c form between themselves ducts 13 and 14. The thickness of the glass sheets is 1 mm and the width of the ducts is also 1 mm. The length of the ducts is 20 mm. Above and below sheets 22a–c there is provided a block 29 and 30 respectively. Blocks 29 and 30 each comprise three glass rods 29a–c and 30a–c respectively fused against each other, rods 29b and 30b being transparent whereas the other rods are made of black glass. In the upper block 29 inlet ducts 23 and 24 and outlet ducts 25 and 26 are drilled as shown. Ducts 23, 25 are in communication with duct 13 and ducts 24, 26 with duct 14. The end surfaces of ducts 13 and 14 and of blocks 29 and 30 are covered by cover glasses 27 and 28 respectively. Blocks 29 and 30, the three glass sheets 22a–c and the cover glasses 27 and 28 are fused together to form a structurally coherent unit. It is obvious that the long optical paths 5 and 6 are formed by ducts 13 and 14 whereas the short optical paths 7 and 8 are formed by sections of these ducts in a direction essentially perpendicular to the direction of the extended optical path.

In FIG. 4 there is shown the through-flow test glass seen from the side of the photocell and in FIG. 5 the through-flow test glass is shown seen from the side of the radiation source.

In FIG. 7 there is shown a further embodiment of a test glass. The test glass shown in FIG. 7 is distinguished from the test glass illustrated in FIGS. 2 – 6 in that the ducts 33 and 34 corresponding to ducts 13 and 14 are provided on different levels. The cross section of the ducts is rectangular enabling measurements to be performed along the direction indicated by arrows A, B and C. The directions A and B are assumed to correspond to the direction of the optical paths 5, 6 and 7, 8 respectively. By choosing suitable mutual ratios between the length, width and height of the ducts it is possible additionally to subdivide the range of sensibility of the instrument. The presupposition in this case is that the radiation source 1 via a mirror arrangement of the like not shown emits light also in the direction indicated by arrow C. Moreover it is to be assumed that fluorescence converters, filters, amplifiers and a logarithm-forming circuit are provided for the two optical paths in the direction of arrows C.

In the embodiment described above it is possible to provide a chopper device in paths 5, 6 and 7, 8. The chopper device operates to pass light beams along the one pair of paths, for example 5, 6, whereas it simultaneously interrupts the light beams in the other pair of paths 7, 8 and vice versa. Thereby the interaction between the light beams in the two optical paths 5, 6 and 7, 8 respectively is reduced. The work frequency of the chopper device is chosen so that the two pairs of optical paths 5, 6 and 7, 8 are eliminated substantially simultaneously.

In FIG. 8 there is shown a block diagram of the electric circuits of the apparatus according to the invention. Lamp 1, which, for example, may be of the type marketed by General Electric in the United States under the designation G4T4/1, is fed via a transformer from the mains as the lamp is of the discharge type its feed circuit also comprises a choke coil and an igniter not shown. The feed voltages for the amplifiers and logarithm-formers are derived from a conventional full-wave rectifier comprising conventional filters and voltage stabilizers (not shown). The logarithm-forming circuit for each of the optical paths 5, 6 and 7, 8 respectively comprises a conventional logarithm-connected operational amplifier, the outputs of these amplifiers being connected to the inputs of a common subtractor.

The embodiment of the invention as described above can be modified and varied in many respects within the frame of the basic idea of the invention.

What we claim is:

1. A fluid analyzer for measuring optical properties comprising first and second elongated flow ducts, one duct being adapted to have a test fluid flowing therethrough and the other duct being adapted to have a reference fluid flowing therethrough, a radiation source for passing radiation through fluid in said ducts, separate detector means for detection of the radiation from said source that has passed through fluid in said ducts, said radiation source being arranged to radiate along at least two optical paths through each flow duct, the first path passing through the corresponding flow duct substantially along the longitudinal direction thereof and the second path passing through the corresponding flow duct transverse to the longitudinal direction thereof, the first optical paths being of equal lengths and the second optical paths being of equal lengths, the length of the first optical paths being substantially greater than the lengths of the second optical paths, and each pair of first and second paths being provided with separate detector means, and evaluation means for determination of the optical properties of the test fluid as compared to the reference fluid along said optical paths in response to the output of said detector means.

2. A fluid analyzer in accordance with claim 1 including a chopper means adapted to pass radiation in the first optical paths while simultaneously interrupting the radiation in the second optical paths and vice versa.

3. A fluid analyzer in accordance with claim 1 wherein said optical paths of different lengths intersect each other in pairs.

4. A fluid analyzer in accordance with claim 3 wherein said first and second flow ducts are formed in a body, each flow duct has a rectangular cross-section and extends substantially between the terminal faces of the body to form said first optical paths.

5. A fluid analyzer in accordance with claim 4 including means defining an inlet and an outlet through a major face of said body for each flow duct.

6. A fluid analzyer in accordance with claim 5 including a third pair of optical paths of mutually equal length extending transverse to the two other pairs of optical paths, at least two pairs of paths being of mutually different length.

7. A fluid analyzer in accordance with claim 6 wherein said third pair of optical paths intersects at least one of the remaining pairs of optical paths.

8. A fluid analyzer in accordance with claim 1 including filter means disposed between the radiation source and an inlet end of the optical paths.

9. A fluid analyzer in accordance with claim 8 including filter means disposed between an outlet end of the optical paths and the detector means.

10. A fluid analyzer in accordance with claim 9 wherein the filter means disposed in the optical paths in one direction are tuned to a distinct wave length and the filter means disposed in the optical paths in a second direction are tuned to a different distinct wave length.

11. A fluid analyzer in accordance with claim 9 wherein the filter means disposed in the various optical paths are tuned to a distinct wave length which is common to all paths.

12. A fluid analyzer in accordance with claim 1 wherein the radiation source has an extended emission surface for simultaneously radiating along said first and second paths.

13. A fluid analyzer in accordance with claim 1 wherein said evaluation means is adapted to substantially simultaneously determine the optical properties of the test fluid as compared to the reference fluid along the different optical paths.

14. A fluid analyzer in accordance with claim 1 wherein the analyzer is adapted to measure radiation absorption.

15. A through-flow test apparatus for measuring the optical properties of fluids comprising a body haivng one flow duct for a test fluid and another flow duct for a reference fluid, each flow duct having a rectangular cross-section and extending substantially between the terminal faces of the body to form a first pair of optical paths of a first length, means defining a second pair of optical paths having a second length substantially different from the first length and extending through limited sections of each flow duct transverse to the flow ducts, and means defining an inlet and an outlet for each flow duct.

16. An apparatus in accordance with claim 15 wherein said body is comprised of a first block of material, a second block of material, three sheets of material secured between said first and second blocks and plates secured to end surfaces of said blocks and sheets of material, said three sheets of material cooperating with said first and second blocks to define said flow ducts, said plates closing the ends of said flow ducts and a section of each block being transparent whereby said second pair of optical paths passes through said transparent sections.

17. An apparatus in accordance with claim 15 wherein each block includes first and second sections formed of a non-light transmitting material and said transparent section, and each of said sheets of material is formed of a non-light transmitting material.

18. An apparatus in accordance with claim 17 wherein each block, each plate and the sheets of material are formed of quartz glass.

19. An apparatus in accordance with claim 16 wherein said sheets of material are approximately one millimeter thick and said flow ducts are approximately twenty millimeters long.

* * * * *